United States Patent
LeFiles et al.

(10) Patent No.: US 11,300,553 B2
(45) Date of Patent: Apr. 12, 2022

(54) SYSTEM AND METHOD FOR CHEMICAL CONTAMINATION DETECTION AND DECONTAMINATION CERTIFICATION

(71) Applicant: Salvus, LLC, Valdosta, GA (US)

(72) Inventors: James LeFiles, Valdosta, GA (US); Clinton Beeland, Valdosta, GA (US); Ron Levin, Valdosta, GA (US)

(73) Assignee: Salvus, LLC, Valdosta, GA (US)

( * ) Notice: Subject to any disclaimer, the term of this patent is extended or adjusted under 35 U.S.C. 154(b) by 493 days.

(21) Appl. No.: 16/454,789

(22) Filed: Jun. 27, 2019

(65) Prior Publication Data
US 2020/0003746 A1    Jan. 2, 2020

Related U.S. Application Data

(60) Provisional application No. 62/690,368, filed on Jun. 27, 2018.

(51) Int. Cl.
*G01N 33/18* (2006.01)
*G01N 33/00* (2006.01)
*G06F 9/54* (2006.01)

(52) U.S. Cl.
CPC ..... *G01N 33/1826* (2013.01); *G01N 33/0029* (2013.01); *G01N 33/0063* (2013.01); *G01N 33/1886* (2013.01); *G06F 9/542* (2013.01); *G01N 2033/184* (2013.01)

(58) Field of Classification Search
CPC .......... G01N 33/1826; G01N 33/0029; G01N 33/0063; G01N 33/1886; G01N 2033/184; G06F 9/542
See application file for complete search history.

(56) References Cited

U.S. PATENT DOCUMENTS

| | | | |
|---|---|---|---|
| 5,504,014 | A | 4/1996 | Lindsay et al. |
| 7,019,637 | B1 | 3/2006 | Johnson et al. |
| 8,388,904 | B1 | 3/2013 | McDaniel |
| 2001/0019844 | A1 | 9/2001 | Kishkovich et al. |
| 2004/0126279 | A1 | 7/2004 | Renzi et al. |
| 2004/0238005 | A1 | 12/2004 | Takayama |
| 2005/0199267 | A1 | 9/2005 | Oakes |
| 2007/0100666 | A1 | 5/2007 | Stivoric et al. |
| 2010/0015601 | A1 | 1/2010 | Gilmore et al. |
| 2011/0065097 | A1 | 3/2011 | Jones, Jr. |
| 2018/0299403 | A1 | 10/2018 | Byrne et al. |

FOREIGN PATENT DOCUMENTS

CN    103675225 A    12/2013

OTHER PUBLICATIONS

International Search Report for PCT/2019/039498, dated Sep. 30, 2019.
Berg, B., et al., "Cellphone-based hand-held microplate reader for point-of-care testing of enzyme-linked immunosorbent assays", ACS Nano (Aug. 2015), vol. 9, No. 8, pp. 7857-7866.
Wang, Y., et al., "A smartphone-based colorimetric reader coupled with a remote server for rapid on-site catechols analysis", Talanta, (Jul. 5, 2016), vol. 160, pp. 194-204.
European Search Report for EP Application No. 19827329.4, dated Jan. 27, 2022.

*Primary Examiner* — Christopher Adam Hixson
(74) *Attorney, Agent, or Firm* — Barnes & Thornburg LLP

(57) ABSTRACT

A portable chemical contaminant detection system and related method is provided. The detection system includes a detector having one or more probes and associated detector circuitry that is in communication with a mobile device. The system is in communication with a remotely located server, where the detection system transmits contaminant detection signals while measuring a fluid from a product or a container of a chemical used on the product. The contaminant detection signals are transmitted in real-time and the detection system receives contaminant level information determined by the server. The server may process data from multiple probes to track multiple contaminants or a single contaminant based on the multiple different probe data from a single detector. The system displays real-time decontamination feedback and displays process completion notification or automatically implements decontamination shut-off. The server tracks location information and contaminant levels for products and communicates with third party certification servers.

20 Claims, 10 Drawing Sheets

SYSTEM AND METHOD FOR CHEMICAL CONTAMINATION DETECTION AND DECONTAMINATION CERTIFICATION

CROSS-REFERENCE TO RELATED APPLICATIONS

This application claims the benefit of U.S. Provisional Application No. 62/690,368, filed Jun. 27, 2018, entitled "SYSTEM AND METHOD FOR CHEMICAL CONTAMINATION DETECTION AND DECONTAMINATION CERTIFICATION, the entirety of which is hereby incorporated herein by reference.

BACKGROUND

Chemical contamination is a problem for industry, agriculture, and consumers alike. For industrial manufacturing companies, confirming the cleanliness of storage, processing, and transfer equipment is a time consuming and expensive endeavor. Consumers have a need to know that the products they buy are free from contamination. For agriculture, off-target application of pesticides is a rapidly growing problem. One factor contributing to such contamination is ineffective cleaning of spray tanks which causes sensitive crops and neighboring flora to be damaged when sprayed (either directly or indirectly) following application of certain herbicides. The problem is growing rapidly with the increased glyphosate tolerance that has developed with hundreds of species of weeds. This is because to prevent their spread and ensure food security for the world, seeds are now utilized that are tolerant to the extremely phytotoxic 2,4-D (2,4-dichlorophenoxyacetic acid) and dicamba (2-methoxy-3,6-dichlorobenzoic acid). Tens of millions of acres have switched to such seeds and tens of millions of acres more are forecasted to be planted with such tolerant seeds. Consequently these seeds will be treated with 2,4-D and dicamba. Concerns about glyphosate has led to expensive litigation with large judgments already awarded. This is going to fuel growth of different pesticides and the desire of consumers to ensure that their food products are free of whichever pesticides are used. With such new technological developments, off-target drift from inadequate spray tank decontamination of herbicides will result in injury to any nearby non-resistant crops and other fauna. Current decontamination practices typically include simply cleaning with copious amounts of ammonia and water (or other commercial cleaning product) and delays caused by the need to send out for lab results verifying adequate decontamination has been achieved. Thus, there exists a need for a safe and effective system and method for chemical detection, decontamination and certification.

SUMMARY

A chemical contaminant detection system and tracking method is provided. According to one aspect, the contaminant detection system includes a portable detector having a probe and detector circuitry for detecting a predetermined contaminant in a fluid sample. The system may also include a mobile device configured to wirelessly receive contaminant detection data from the portable detector and transmit the contaminant detection data from the portable detector to a remotely located processor in real-time. The mobile device may be further configured to receive and display on the mobile device real-time contaminant level data processed by the remote processor from the contaminant detection data. In different implementations, system is mobile and sized to be hand-held and the detector may include plurality of probes each configured to detect a different contaminant. The system may be configured to receive the fluid sample from a rinsate collection apparatus connected to a vessel during a cleaning process of the vessel. Additionally, the mobile device may receive and display a cleaning completion notification received from the remote processor in response to determination by the remote processor that the transmitted contaminant data indicates a contaminant level in the fluid sample has reached a predetermined level.

According to another aspect, a method of determining the level of chemical contaminant in a fluid sample includes introducing a probe of a portable detector system into a fluid sample to detect at least one contaminant in the fluid sample and wirelessly transmitting contaminant detection signals from detection circuitry in communication with the probe to a mobile device of the portable detector system. The method further includes transmitting, in real-time, the contaminant detection signals from the mobile device to a remotely located processing system and then receiving, in response to the transmitted contaminant detection signals, real-time contaminant level data processed by the located processing system from the contaminant detection signals. The mobile device displays the real-time contaminant level data to a user on a display. In various implementations, the method may include taking the fluid sample from an agricultural spray tank, industrial mix tank or transportation tank. Additionally, in some embodiments the mobile device, in response to receiving a cleaning completion message from the server, transmits a shut-off command configured to automatically shut of equipment being used in the cleaning process of a vessel.

According to yet another aspect, a method for managing contaminant certification data based on real-time testing of contaminants at local stages of production of a product is provided. The method may be executed in a system having a plurality of product handling facilities at different geographic locations, where each of a plurality of portable contaminant detection systems located at a respective one of the product handling facilities is in communication with a central contaminant tracking server. In this system, the central contaminant tracking server receives user and device identification from a portable contaminant detection system at one of the plurality of product handling facilities. The server also receives real-time contaminant detection data from the portable contaminant detection system. The server determines a contaminant type and a current contaminant level data from received the contaminant detection data, and then transmits the current contaminant level data to the portable contaminant detection system for display at the portable contaminant detection system. Determining the contaminant type and transmitting the current contaminant level data is performed in real-time and, in response to determining that the current contamination level has reached a desired threshold, the server transmits a completion notification to the portable contaminant detection system.

DETAILED DESCRIPTION

Figure 1:
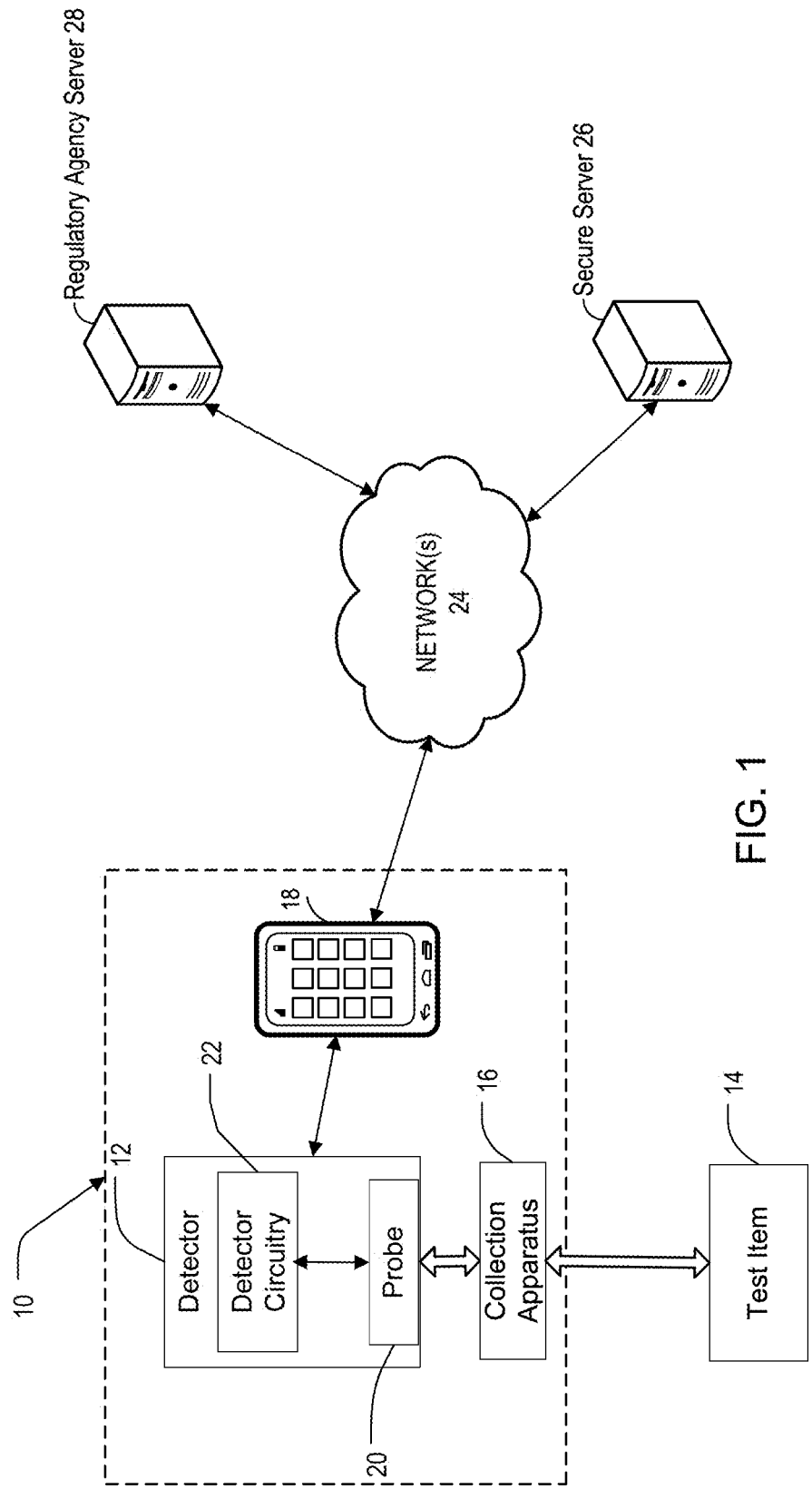
FIG. 1 illustrates a system for real-time chemical contamination detection and decontamination certification according to one embodiment.

In order to address the need for faster and more reliable handling of chemical cleaning and decontamination, and to provide for verification or certification of a product's reduced exposure to chemicals or other contaminants tracked from production to market, on-site portable contamination testing systems and methods are described herein, whether at a chemical production facility, farm, food processing plant or further downstream in the food distribution path at the retail or consumer location. There is increasing interest in the effects of materials/chemicals used in the production of products and in particular the production of food. This interest in food contaminants has led many consumers to request "Organically Grown" food. However, many consumers don't have the economic ability to purchase organically grown food as it tends to cost more than traditional agriculture. In addition, current methods to grow organically are unlikely to sustain the growing world population as the methods produce lower yields per acre which is one of the biggest drivers in cost. Pesticide residue is determined during the registration process with the U.S. Environmental Protection Agency (EPA) however field testing is generally only done during the original registration process for organic certification and for any subsequent requirements.

Regulation, environment, and sustainability are increasing concerns globally. In agriculture this is primarily focused on naturally occurring toxins (alflatoxin, etc.) pesticides. Regulations continue to put pressure on the use of pesticides and the control of toxins. For environmental and sustainability industry continues the development of newer chemistries and the reduction of more hazardous chemistry.

In industry, the increase in flexibility and reduction in capital creates many multi-use systems, vessels, and transportation systems. This increases the potential for cross contamination through failure to clean the prior vessel effectively prior to loading with the next chemistry or product. Technical solutions are provided herein that allow the determination of contamination in a short enough time, and allow informed decision making by people with no advanced chemical analytical knowledge. People with advance analytical knowledge are currently using technical solutions that impose significant costs in terms of time.

Methods and systems are provided herein to address the need to certify production equipment and perform tests as well provide results in real-time. Additionally, methods and systems for using this real-time contamination detection to manage product flow and reliably track and verify a product's exposure to chemicals or other contaminants throughout a complete supply chain are disclosed.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur.

As used herein, the term "chemical contaminant" refers to any air-based, liquid, or solid chemical the presence of which needs to be measured. Chemical contaminants include, but are not limited to, inorganic contaminants (IOCs), volatile organic contaminants (VOCs), synthetic organic contaminants (SOCs), organic chemicals, inorganic chemicals, or disinfection by-products. Chemical contaminants include all common agricultural chemicals used on or around a crop such as, for example, herbicides, pesticides, and fertilizers. Specific agricultural chemical contaminants include 2,4-D (2,4-dichlorophenoxyacetic acid) and dicamba (2-methoxy-3,6-dichlorobenzoic acid). As used herein, the term "vessel," "container," and "tank" may be used interchangeably and also includes surrounding support equipment such as pipes, hoses, and pumps.

A system for chemical decontamination detection is provided. The system is mobile or portable for ease of use in various environments. The system may be hand-held. The system may include a variety of components as provided herein within a rugged, stable shell or case. The system may also be powered via alternating current or direct current. The direct current may be provided by a battery such as, for example, or more lithium or alkaline batteries.

The system may be equipped with one or more software packages loaded within. The software may be electronically connected to the various system components as provided herein. The software may also be electronically integrated with a display for viewing by a user. The display may be any variety of display types such as, for example, a LED-backlit LCD. The system may include a memory component such that operating instructions for the system may be stored and all data related to detected contaminant levels may be stored or archived for later retrieval or downloading onto a workstation or smartphone.

According to one embodiment, the system may include a collection component. The collection component may include an inlet for fluid collection. The collection component may be a physical extension of sampling area with an electronic signal connection to a detector component as described herein. The collection component may include or be connectable to a probe designed to generate a signal when exposed to a specific compound.

According to one embodiment, wherein the wireless signal is processed with specialized algorithms based on chemistry, physics, and/or quantum mechanics by a remote server and the output data is nearly instantaneously wirelessly transmitted back to the mobile system from the remote server certifying an acceptable level of chemical contaminant when achieved. According to one embodiment, the sensing unit is mobile and sized to be hand-held. According to one embodiment, current versions of the algorithms appropriate to the contaminants being tested are loaded on the sensing unit to allow it to operate independently of wireless communications. The mentioned algorithm may include the ability to combine inputs from sensors based on differing technologies to identify substances that individual sensing technologies would typically not be able to distinguish.

According to one aspect, a method of determining the level of chemical contaminant in a sample is provided. The method includes the steps of collecting a fluid sample and detecting any chemical contaminant in the fluid sample. In different embodiments, the fluid sample may be taken from an agricultural spray tank, an industrial mix tank, a transportation tank or any of a number of other fluid carrying vessels. According to one embodiment, the method further includes the step of transmitting a signal regarding the level of contaminant in the sample to a device at a remote destination. The remote destination device may be a locally operated mobile or portable device, such as a smart phone, tablet device, pad, or laptop computer. In other embodiments, the remote destination may be a stand-alone or networked computer, cloud device, or server accessible via a local portable device. According to one embodiment, when the signal is transmitted wirelessly to a remote server, a return signal is transmitted to the system providing certification when an acceptable level of chemical contaminant is achieved.

According to one embodiment, the system as provided herein includes a detector. The detector may utilize gold catalyzed chemiluminescence immunoassay, immunoassay in microfluidics, electrochemical immunoassay, or dip-stick immunoassay. According to one embodiment, the detector may utilize an interferometric sensor based on a planar optical waveguide. According to one embodiment, the detector may utilize immunoassays on top of the waveguide for detection of one or more chemical contaminants. According to one embodiment, the detector may include one more polymers. According to on embodiment, the detector may include, or function based on, an enzyme-linked immunosorbent assay. According to one embodiment, the detector may utilize or more polypeptides, nucleic acids, antibodies, carbohydrates, lipids, receptors, or ligands of receptors, fragments thereof, and combinations thereof such as that set forth in U.S. Patent Pub. No. 20080138797, the entirety of which is hereby incorporated by reference herein. According to one embodiment, the detector may provide a visible color change to identify a particular chemical contaminant. According to on embodiment, the detector may include a reference component that provides secondary confirmation that the system is working properly. Such secondary confirmation may include a visual confirmation or chemical reference that is detected and measured by the detector.

According to one embodiment, the detector includes at least one filter. The filter may be located between the collection and component and the detector. According to one embodiment, the at least one filter includes activated charcoal. According to one embodiment, the at least one filter includes at least one resin such as anion exchange resin, cation exchange resin, softener resin, or a combination thereof.

According to one embodiment, the detector analyzes a fluid sample, such as a gas, a liquid or any combination thereof. The fluid may be a rinsate that flows from any fluid source. The fluid may also be a water sample. The fluid may include one or more chemical contaminants that require detection and certification of a certain level. According to one embodiment, the detector is calibrated to detect certain levels of at least one fluid, such as a liquid, gas or aerosol, chemical contaminant. According to one embodiment, the detector is calibrated to detect certain levels of specific agricultural chemicals such as, for example, 2,4-D (2,4-dichlorophenoxyacetic acid) and dicamba (2-methoxy-3,6-dichlorobenzoic acid). The detector may be sensitive down to a parts per million level. In some implementations, the detector may also be sensitive down to a parts per billion level. The differentiation between typically difficult to distinguish substances, such as 2,4-D and dicamba, may be achieved in the disclosed real-time system because of the ability of this technology to combine the signals from two or more types of sensors. By gathering and transmitting real-time sensor data from more than one type of probe, a computation layer of a remote server in the disclosed system may use an algorithm to interpret the signals in direct real-time comparison for immediately identifying and quantifying the concentration of different compounds. In alternative embodiments, the detector system may make the analysis and calculations itself without the use of the processing power of the remote server.

The fluid introduced to the system described herein may be obtained from various fluid sources. The fluid source includes any vessel or container that may come internally in contact with a chemical contaminant. The system as provided herein may be placed in fluid communication with the vessel so as to detect and certify acceptable contaminant levels in real time. Fluid communication may be established via a tube or other conduit that allows any fluid containing at least one chemical contaminant to come in contact with, or flow through, the system as provided herein.

According to particular embodiment, the fluid source may be a liquid source such as an agricultural spray tank. Such a spray tank may be located on a tractor (or other agricultural implement), in a field/crop area, at a farmer's cooperative or other location where a farmer will utilize spray tank. Specific embodiments of spray tank detection are provided in Examples 1 and 2 below. According to the various embodiments described herein, the system and method may reduce the time typically required for spray tank decontamination, minimize the need to utilize (and store) large volumes of ammonia and other commercial tank cleaners, reduce dependency of the farm equipment operator to execute decontamination processes without benefit of knowledge of the point completion, eliminate the application of improperly decontaminated spray tank rinsate on labeled crops, and/or reduce legal risk to the farm equipment operator by providing documentation of spray tank decontamination.

According to one particular embodiment, the fluid source includes an industrial/commercial vessel. Such a vessel may be located within or around a manufacturing facility that utilizes any one or more of a variety of chemical contaminants at food, chemical, or biological product manufacturing operations facility or at a famer's cooperative. In another embodiment, the fluid source includes a shipping container that stores and transports a fluid chemical. The shipping container may be located on a truck, train, or other means of transportation. The shipping container may also be located on or around shipping dock.

According to one embodiment, the detector may be optionally equipped to analyze additional environmental factors such as, for example, particulate matter (viable and otherwise), temperature, air flow, and humidity.

The system as provided herein may also include a transmitting component. The transmitting component may be in electronic signal communication with the detector component. The transmitting component sends or transmits a signal regarding real-time chemical contaminant level data. Such data may provide evidence of chemical contaminant removal and/or inactivation and reduces. The transmission of such data may include real-time transmission via any of a number of known communication channels, including packet data networks and in any of a number of forms, including text messages, email, and so forth. Such real-time transmission may be sent to a remote destination via a wireless signal. The wireless signal may travel via access to the Internet via a surrounding Wi-Fi network. The wireless signal may also communicate with a remote destination via Bluetooth or other radio frequency transmission. The remote destination may be a smart phone, pad, computer, cloud device, or server. The server may store any data for further analysis and later retrieval. The server may analyze any incoming data using artificial intelligence learning algorithms or specialized chemical, physical, or quantum mechanical expertise programmed into the server and transmit a signal back to the system confirming an acceptable of chemical contaminant was achieved. According to one embodiment, the system or server may be equipped with, or have access to, contaminant level reference data such that certification may be received by the system alerting a user that an acceptable level of chemical contaminant has been achieved. An acceptable level of chemical contaminant may be any predetermined level that is set by a rule-making authority such as, for example, the Environmental Protection Agency (EPA) or by a law-making authority.

According to one embodiment, the system includes a wireless data link to a phone line. Alternatively, a wireless data link to a building Local Area Network may be used. The system may also be linked to Telephone Base Unit (TBU) which is designed to physically connect to a phone jack and to provide 900 MHz wireless communications thereby allowing the system to communicate at any time the phone line is available.

A method of determining the level of chemical contaminant in a sample is also provided. The method includes the step of collecting a sample. The sample may be from any fluid source as provided herein. According to a particular embodiment, the sample is taken from an agricultural spray tank, industrial/commercial mix tank, or transportation tank. The method further includes the step of detecting any chemical contaminant in the sample. The method utilizes at least one detector as described herein which is in electronic communication with the transmitting component.

The method further includes the step of displaying the chemical contaminant levels to a user of the system. The step of displaying the contaminant levels may be carried out via projecting any real time data on a screen as described herein.

The method may further include the step of transmitting a signal regarding the level of contaminant in the sample to a destination. The step of transmitting may occur via a wireless signal, Bluetooth, radio frequency, local area network, or via a traditional phone line. The signal from the system includes data related to the level of chemical contaminant in the sample and diagnostic information about the sensor and the parameters around its use. The destination may be smart phone, pad, computer, cloud device, or server. The destination may, in turn, communicate or signal the system that an acceptable level of chemical contaminant is achieved or that the level is unacceptable. In the event the level of chemical contaminant is acceptable, the destination may communicate a certification of acceptable chemical contaminant level. The certification may be based on environment standards promulgated by an authority such as, for example, the EPA. The certification may also be simultaneously submitted to a local or national authority such as, for example, the EPA. According to an alternative embodiment, the destination is a smart phone, pad, computer, cloud device, or server under the custody of a local or national authority such as, for example, the EPA.

The method may further include the step of disposing of the sample per legal requirements. Such legal requirements assure that any sample still containing unacceptable levels of chemical contamination are disposed of properly so as not to cause harm to a user or the environment.

A method can be integrated with a process of decontaminating a vessel. The method may also include the step of adding a cleaning composition to the vessel to form a rinsate. According to such an embodiment, the vessel may be in fluid communication with a vessel pump for moving the cleaning composition through the vessel and out to the system. The method may also include the step of attaching a collection apparatus to the vessel to that any rinsate exiting the vessel is channeled directly to the system for analysis. The method may also include the step of monitoring the detector until the detector indicates an acceptable level of chemical contaminant within the rinsate. According to one embodiment, the tank cleaning composition includes at least one chemical agent and water. Also, the process may further include the step of disposing of the rinsate per legal requirements.

Referring now to FIG. 1, an embodiment of a contaminant detection system 10 is shown. The system 10, includes a detector unit 12, also referred to herein as a detector, configured to sample a test item 14 for a detection target, such as a chemical contaminant, via a collection apparatus 16. The collection apparatus 16 may be any of a number of fluid pathways and devices configured to route the substance from the test item 14 into contact with the probe 20 of the detector 12. For example, the collection apparatus 16 may be a liquid conduit, or liquid conduit and pump arrangement when the test item is a liquid. Alternatively, the collection apparatus may be a gas conduit, or a fan and gas conduit if the test item is a gas. The collection apparatus 16 may be integrated with the detector unit 12, or may be removable connectable to the probe 20 of the detector unit.

The detector 12 unit may communicate the raw data or findings of the probe 20 in real-time with a mobile device 18. The mobile device 18 may include logic stored in local memory on the mobile device to interpret the raw data and findings directly, or it may communicate over a network 24 with a remotely located server 26 to transfer the raw data or findings and request interpretation by logic located at the server 26. The mobile device 18 may be a handheld device, such as a smart phone, tablet, laptop computer that permits a user access to the real-time measurements of the probe and their real-time interpretation by a remote server 26. As described in greater detail below, the real-time interpretation of contaminant levels may be displayed to the user on the mobile device with an indication of whether the amount of contaminant or purity of a substance is in a desired range. In some embodiments, the information received back from the server 26 may include notification that a cleaning process is complete or that a process requiring a certain purity may continue, and/or may include instructions that the mobile device passes on to local cleaning or processing equipment to cease or begin operations automatically based on the detected aspects of the contaminant or substance. Additionally, the remote server may concurrently communicate results and verification of completed decontamination processes to a third party server, such as a regulatory agency server 28, insurer, or other interested party.

In the context of chemical production, the detector 12 may be configured to look for a desired detection target and thus may be used to monitor or sample a desired substance for purity. In the context of cleaning or re-use of a vessel for the same or a different substance, the detector unit 12 may be configured to look for a particular contaminant or contaminants. In this latter arrangement, the detector unit may be used in conjunction with, or incorporate, cleaning equipment used to clean a vessel containing the test item.

The target item for testing may be any of a number of items or locations. For example, the target item may be a vessel, such as a chemical plant vessel, a tank car or tank truck, farm equipment or vessels, soil, food, an agricultural field, and so on. The form of the desired substance or contaminant being detected in or on the target item may be a fluid, such as a gas, a liquid or a combination of a gas and liquid. Additionally, the desired substance or contaminant may include one or more pesticides, pathogens, pollutants, beneficial organisms and other substances.

The detector unit 12 may include a probe 20 in communication with detector circuitry 22. The probe 20 may be a single purpose probe 20 designed for detection of one type of desired substance or contaminant, may include a plurality of probes 20 each designed to detect a different respective substance or contaminant, or may include one or more probes 20 each designed for detection of more than one type of substance or contaminant. As will be evident in the examples provided below, the probe 20 may be placed in contact with, or proximity to, the target item being measured via the collection apparatus. The detector circuitry 22 may be configured to translate probe information into electrical signals or data in a predetermined format and to transmit the electrical signals or data over a wireless (e.g., Bluetooth) or wired connection to the mobile device. The detector circuitry may perform some or all of any data adjustment necessary for the sensed information from the probe 20, for example adjustments to the sensed information based on probe type or age, or may simply pass the data on for transmission to the mobile device 18.

Figure 2:
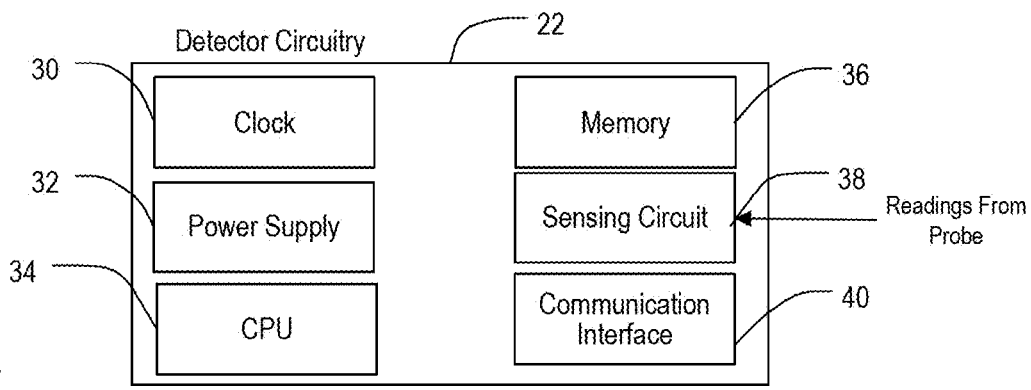
FIG. 2 illustrates one embodiment of detector circuitry that may be implemented in the detector of FIG. 1.

As illustrated in FIG. 2, an embodiment of the detector circuitry 22 is shown. The detector circuitry 22 included in the detector unit 12 may include a power supply circuit 32 (battery or AC), an internal clock 30 for tracking measurement times for the associated probe 20, a sensing circuit 38 arranged to receive measurements or readings from the probe 20, and a communication interface 40 for communicating with the mobile device 18. The detector circuitry 22 may include a central processing unit (CPU) 34 or other controller, along with a memory 36 for storing executable instructions for operating the detector unit 12 and storing information sensed from the probe 20. The probe may include chemical, electrical, optical, and/or other sensitivity and is configured to translate the sensed information into electrical signals for the sensing circuit B5 to recognize. The CPU 34 may control the detector unit to transmit the data immediately from the sensing circuit 38 to the mobile device 18 via the communication hardware B6. Alternatively, the sensing circuit 38 may store the sensed information in the memory 36 and the CPU 34 may cause the sensed information to be transmitted at predefined intervals via the communication hardware 40. In yet other implementations, the CPU 34 may only direct the sensing circuit 38 to sample the probe 20 information at predetermined time intervals (e.g. a fixed number of milliseconds apart) and transmit the sensed information at the same, or a different, interval via the communication interface 40.

Figure 3:
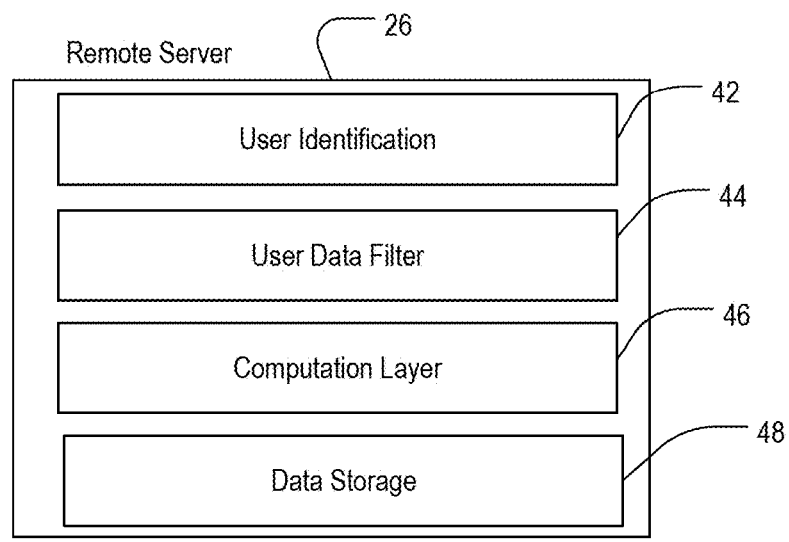
FIG. 3 illustrates an embodiment of functional layers that may be implemented in the remote server of FIG. 1.

Referring to FIG. 3, the remote server 26 may be a computer configured as a web page host providing web-enabled services and including functional layers such as user identification management 42, a user data filter 44, a computation layer 46 and a data storage layer 48. The user identification management 42 may be a user authentication function to verify that authenticated users and mobile devices are properly screened and allowed access. The computation layer 46 may include functionality that receives raw or partially processed data from a detector 12 via a mobile device 18 and determines the type and level of contaminant associated with the received data based on predetermined algorithms. Although the computation layer 46 functions of the server 26 may also, or alternatively, be stored in the mobile device 18 in certain embodiments, an advantage of real-time transmission of the detected data to the server 26 for processing is that greater processing power may be applied to more quickly translate the received data into contaminant level determinations. Also, the central location of the computation layer 46 in the remotely located server 26 provides a centralized location with which to update and control the techniques used to translate the data from the various detectors 12. In different implementations, the computation layer 46 may implement artificial intelligence learning algorithms or specialized chemical, physical, or quantum mechanical expertise programs to process the real-time data into contaminant levels for immediate transmission from the server 26 to, and display on, the mobile device 18.

Figure 4:
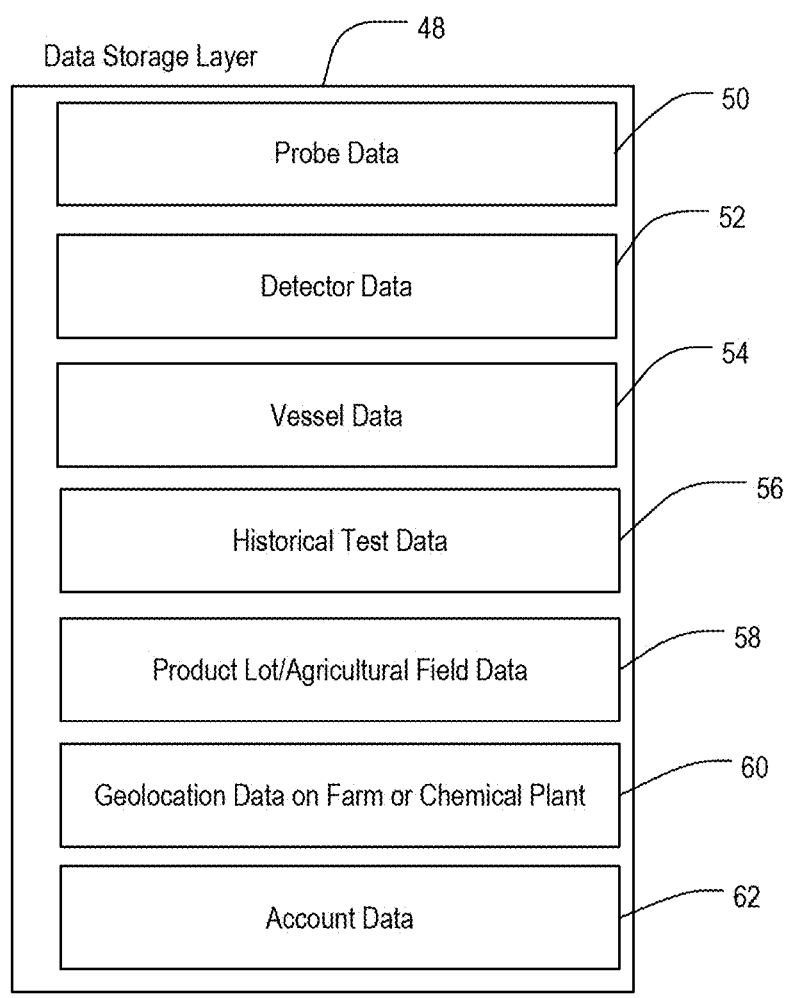
FIG. 4 is a diagram illustrating the types of data records that may be stored in the data storage layer of the remote server of FIG. 1

The data storage layer 48 may include data on users, devices, device types, and, as discussed in greater detail below, a history of contaminant test results for both vessels used in a production process and products, such as crops or processed foods that have been in contact with the vessels or the contents of the vessels used in the production of that crop or food. Referring now to FIG. 4, an example of the data types stored in the data storage layer of the remote server is shown. The data storage layer may include probe data 50 for the various probes 20 that are associated with detectors 12 in the field and registered with the system. The probe data 50 may include information about each specific probe 20, such as the type and age of the probe (e.g. the number of tests run with the probe and the in service data of the probe). The probe data 50 may additionally include information on the probe's technology, including the substances testable by the probe alone or in combination with other probes, probe age calibration curves for use by the computation layer to adjust data received from the probe to account for potential effects of aging on the measurements, and probe technology interaction algorithms, for example this information may be an algorithm such as described herein to use multiple probe data received concurrently to differentiate for detection of a compound/contaminant that may not be directly discernible by a single probe. Similarly, detector data on the detector 12 itself may be stored in the data storage layer 48 of the server 26. The detector data 52 may include serial number and MAC ID for the specific hardware, identification of authorized users, the location of the last use of the detector and the account ID associated with the detector 12. Vessel data 54 on the vessel being tested and tracked may be included in the data storage layer 48 of the server 26. The vessel data 54 may include the unique identifier of the vessel and the account ID of the account associated with that vessel.

To provide improved tracking and certification of decontamination of vessels and the history of contact with vessels and contaminants, the data storage layer 48 also may include historical test data 56 received from different detectors 12 and associated with specific containers, product lots and so on. The historical test data 56 may include data for each test run, such as: a record that probe compatibility was confirmed for each test, the time stamps and detector values received for the test, the age of probe corrections and probe interaction factors determined for the test, and the calculated values for the contaminant or substance detected. Additionally, historical test data 56 for each test run may include location and identification information, such as the geolocation of the detector 12 at time of test, the identifier information for the vessel, detector, user, and probe(s) 20 for that test run, and the account ID of the entity for whom the tests are being run and tracked. In order to link the individual tests to a common crop or product, the historical test data 56 may also include data 58 for the lot or agricultural field tested, such as the time stamps of the test, the lot/agricultural field bar code (or other unique identifier), the customer lot number of the food product and a test identifier number. When the testing is performed at a food processing plant, the server 26 may also include the lot number, food description and or food pack universal product code (UPC) or other identifier and link that to the history of testing of the food and chemical exposure of the food that went into that lot of processed food. Geolocation information 60 on the farm or chemical plant at which testing has been or will be performed may also be stored in the data storage layer 48. The farm or chemical plant information 60 may include geofencing coordinates, such as perimeter coordinates for a field or plant, along with a description of the field or plant and the customer ID associated with that facility. Account data 62 may be stored in the data storage layer as well, including user IDs and associated information associated with each account that utilizes the system.

Any of a number of probe types and technologies may be used in different embodiments. An example of a probe type that maybe used to differentiate between often difficult to differentiate compounds such as 2,4-D and dicamba may include probes that are an interferometric biosensor type, such as an a molecularly imprinted polymer (MIP) or and an antibody assay probe. These probes may be part of a detection system 10 that produces real-time readings for which the rate of change of those readings output by the probes may be measured with the disclosed detection system 10. For example the probes may each generate a diffraction or interferometric pattern and the changes in that pattern are detected and analyzed by the computation layer or locally at the mobile device 18 of the detection system 10, and are translated into a contaminant level, and not just a presence or absence of the contaminant. In one implementation, the contaminant level may be proportional to a rate of change of the diffraction pattern measured, such that an integration of the rate of change in the diffraction pattern may be used to determine concentration levels. This calculation may take place locally at the mobile device 18 or remotely at the server 26.

Referring now to Examples 5-7 below, some embodiments of the use of the system of FIG. 1 in the specific context of decontamination of spray tanks are described.

Example 1

Figure 5:
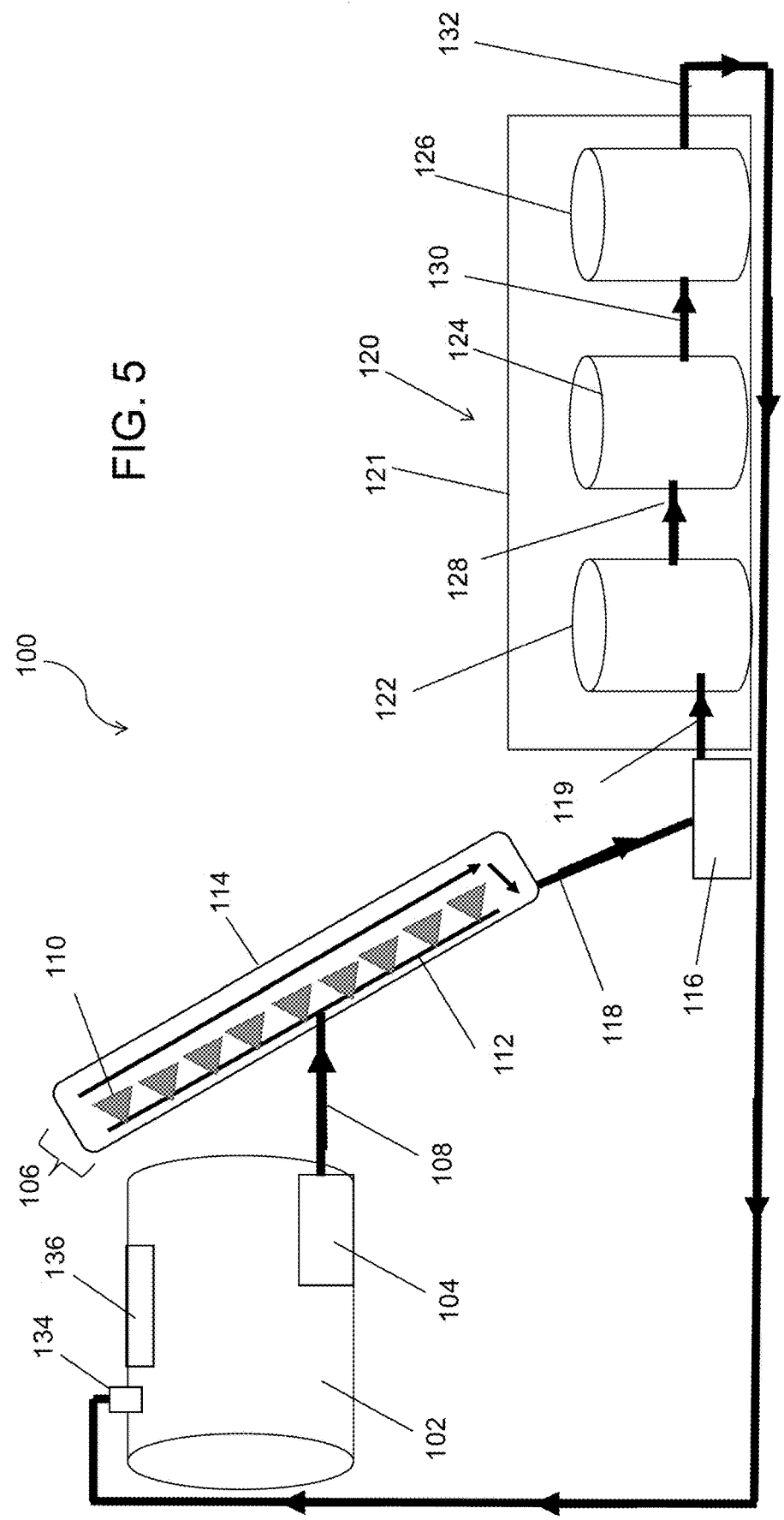
FIG. 5 illustrates a system for the decontamination of an agricultural spray tank according to one embodiment.

FIG. 5 illustrates a system for the decontamination of an agricultural spray tank according to one embodiment. The system 100 includes at least one spray tank 102. The spray tank 102 may be of any size and shape as is agriculturally acceptable to spray herbicide on a crop. As illustrated, the spray tank 102 includes at least one feed pump 104 connected to a spray boom 106 by a main feed line 108. The feed pump 104 may be located outside of the spray tank 102 (not shown). The main feed line 108 may be fabricated from any material that is chemical, weather, and ozone resistant yet able to transport low pressure water-based agricultural fluids. According to one embodiment, the main feed line 108 is fabricated from ethylene propylene diene monomer (M-class) rubber.

The spray pump 104 is of an acceptable size to move one or more gallons of rinsate per minute out of the tank 102 and to through the main feed line 108. The spray pump 104 may be powered via a battery pack (not shown) located within or external to the spray pump 104. The battery pack may be rechargeable and portable. The spray pump 104 may also be powered via a direct current from a surrounding source (such as on a tractor or generator or surrounding building).

The spray boom 106 includes a plurality of nozzles 110 connected by a spray boom manifold 112. The spray boom 106 may be of any agriculturally acceptable size and include any number of nozzles 110. The nozzles 110 and spray manifold 112 are fabricated from any agriculturally acceptable material that may withstand the demands of spraying herbicide on crops.

During use of the system 100, the spray boom 106 is enclosed within a rinsate collection apparatus 114. The rinsate collection apparatus 114 is of a size and shape to substantially or fully enclose the spray boom 106. According to an alternative embodiment, the rinsate collection apparatus 114 may partially enclose the spray boom 106. According to either embodiment, the rinsate collection apparatus 114 collects rinsate discharged from the nozzles 110 during use of the system 100. The rinsate collection apparatus 114 may be fabricated from any acceptable material that collects and directs rinsate. According to one embodiment, the rinsate collection apparatus 114 is fabricated from a solid, substantially non-flexible material that is substantially cylindrical shape such, for example, a pipe (e.g., polyvinyl chloride). According to one embodiment, the rinsate collection apparatus 114 is fabricated from a waterproof material. According to one embodiment, the rinsate collection apparatus 114 is fabricated from a flexible material. According to one embodiment, the rinsate collection apparatus 114 is fabricated to form a bag or bladder that may be unfolded or unpackaged at the time of use and dried upon completion of decontamination. According to such an embodiment, the bag or bladder may be attached to the spray boom 106 via at least one hook and loop fastener.

The rinsate collection apparatus 114 is connected to a feed pump 116 via a first discharge line 118. The feed pump 116 causes rinsate from the rinsate collection apparatus 114 to move through the first discharge line 118 through the feed pump 116 and into a rinsate treatment unit 120 via a second discharge line 119. The feed pump 116 is of an acceptable size to move one or more gallons of rinsate per minute out of the rinsate collection apparatus 114 and to through the second discharge line 108. The feed pump 116 may be powered via a battery pack (now shown) located within or external to the feed pump 116. The battery pack may be rechargeable and portable. The feed pump 116 may also be powered via a direct current from a surrounding source (such as on a tractor or generator or surrounding building). Each of the first and second discharge lines (118, 119) are fabricated from any material that is chemical, weather, and ozone resistant yet able to transport low pressure water-based agricultural liquids such as, for example, ethylene propylene diene monomer (M-class) rubber.

As illustrated, the discharge line 119 connects the feed pump 116 to at least one filter 122 (e.g., a first filter) within the rinsate treatment unit 120. The rinsate treatment unit 120 further includes an optional second filter 124. The rinsate treatment unit 120 optionally includes a detector 126 located within the rinsate treatment unit 120. A first treatment line 128 connects the first filter 122 to the second filter 124. A second treatment line 130 connects the second filter 124 to the detector 126. A decontamination line 132 connects the detector 126 back to an inlet 134 (or cap 136) on the spray tank 102. Each of the first and second treatment lines (128, 130) and decontamination line 132 are fabricated from any material that is chemical, weather, and ozone resistant yet able to transport low pressure water-based agricultural liquids such as, for example, ethylene propylene diene monomer (M-class) rubber.

The entire rinsate treatment unit 120 may be portable as well as sized to be held and operated in the operator's hand. The rinsate treatment unit 120 may be formed of a housing unit 121 that encompasses the filter(s) (e.g., 122 and 124) and, optionally, the detector 126. The housing unit may be made of any acceptable material capable of enclosing and securing one or more filters (e.g., 122 and 124) and, optionally, a detector 126.

The at least one filter 122 (or first filter) aids the removal or deactivation of herbicides present in the rinsate. According to one embodiment, the filter 122 contains activated charcoal. According to one embodiment, the activated charcoal is in powder form and exhibits a high affinity for organic compounds such as herbicides. According to one embodiment, the filter 122 contains at least one pound of activated charcoal for each 50 gallons of rinsate passed through the system. According to one embodiment, the filter 122 contains a fibrous form of activated carbon. According to another embodiment, the filter 122 contains at least one resin. Suitable resins include, but are not limited to, anion exchange resins, cation exchange resins, and softener resins.

The optional second filter 124 further aids the removal or deactivation of herbicides present in the rinsate. According to one embodiment, the second filter 124 performs an ozonation process. According to one such embodiment, the ozone is injected as small bubbles in the passing rinsate and then filtered. According to another embodiment, the second filter 124 includes an ultraviolet purification component. The ultraviolet component may be utilized alone or in addition to the ozonation process. According to one embodiment, the filter 124 includes an ultraviolet light source (lamp) enclosed in a protective transparent sleeve. According to one embodiment, the light source may be mounted such that rinsate passes through a flow chamber in the filter 124 and is exposed to the ultraviolet light rays.

The detector 126, which may be all or part of the detector 10 of FIG. 1, analyzes the rinsate as the rinsate passes through the detector 126. According to one embodiment, the detector 126 provides real time readings regarding herbicidal levels within the rinsate. According to one embodiment, the detector 126 confirms and provides documentation of effective cleanout based on herbicidal levels in the rinsate. Such documentation may include real-time transmission of data via email, storage on an internal or external drive, or printout. Such documentation provides evidence of herbicide removal and/or inactivation and reduces or eliminates liability on the farm operator for damaged crops caused by herbicidal treatment.

According to one embodiment, the detector 126 may utilize gold catalyzed chemiluminescence immunoassay, immunoassay in microfluidics, electrochemical immunoassay, or dip-stick immunoassay. According to one embodiment, the detector 126 may utilize an interferometric sensor based on a planar optical waveguide. According to one embodiment, the detector 126 may utilize immunoassays on top of the waveguide for detection of one or more herbicides. According to one embodiment, the detector 126 may include a reference component that provides secondary confirmation that the system 100 is working properly. Such secondary confirmation may include a visual confirmation or chemical reference that is detected and measured by the detector 126. According to one embodiment, the detector 126 is calibrated to detect certain levels of at least one herbicide. According to one embodiment, the detector 126 is calibrated to detect certain levels of specific herbicides such as, for example, 2,4-D (2,4-dichlorophenoxyacetic acid) and dicamba (2-methoxy-3,6-dichlorobenzoic acid).

Example 2

Figure 6:
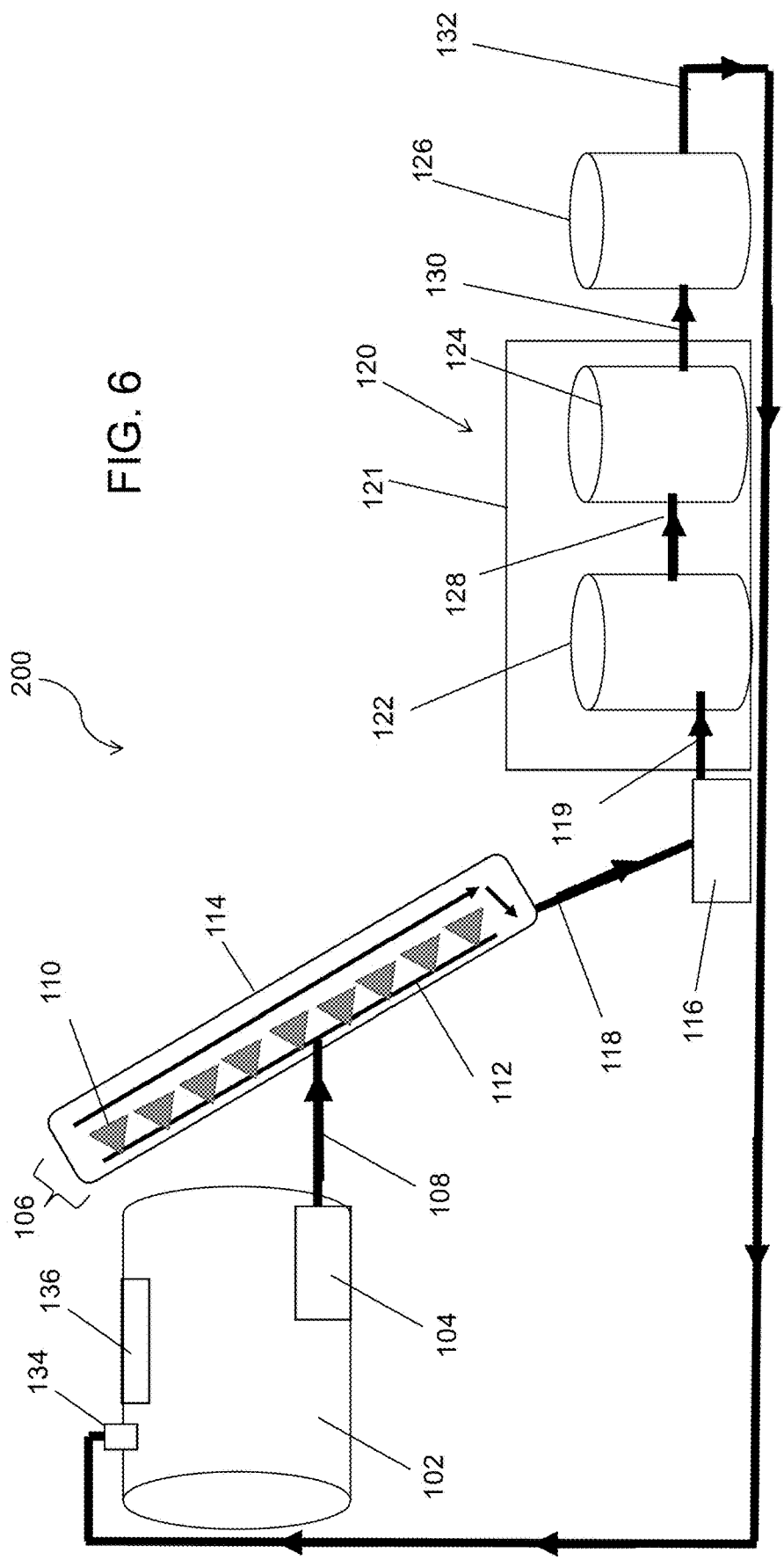
FIG. 6 illustrates a system for the decontamination of an agricultural spray tank according to an alternative embodiment.

FIG. 6 illustrates a system for the decontamination of an agricultural spray tank according to an alternative embodiment. The system 200 includes the same components as illustrated in the embodiment of FIG. 5. The detector 126, however, is located outside the rinsate treatment unit 120. The detector 126 may be portable as well as sized to be held in the operator's hand.

Example 3

Figure 7:
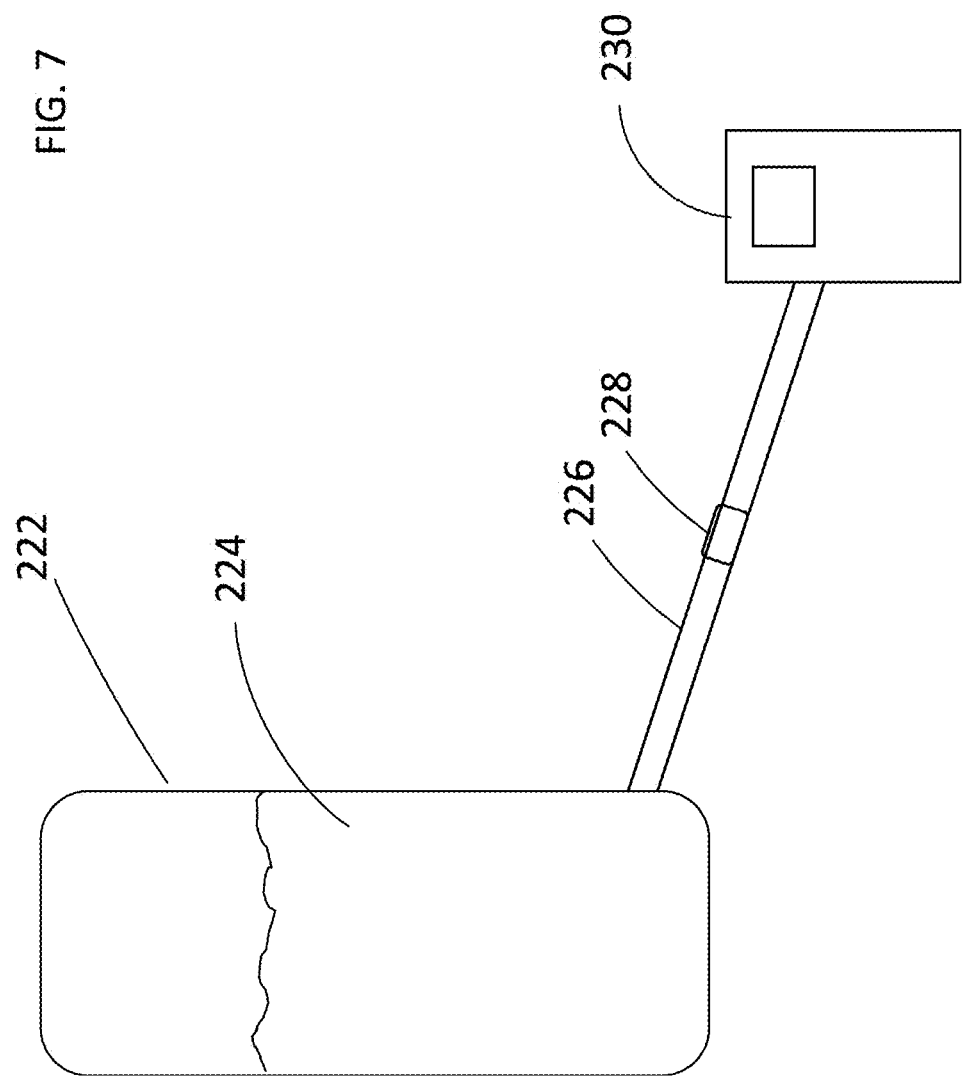
FIG. 7 illustrates an embodiment of a system for the decontamination of a vessel at a production facility

FIG. 7 illustrates an embodiment of a system for the decontamination of a vessel 222. As illustrated, a tube or other conduit 226 is introduced to the vessel 222 to place a detection system 230. A pump 228 may be utilized with the conduit 226 to aid in moving the fluid 224 from the vessel 222 to the detection system 230. The vessel 222 may be an industrial/commercial mix tank or transportation vessel of any type. In the example of FIG. 7, the cleaning process may be a default cleaning process (time and amount of cleaning agent pre-determined) and the measurement by the detection system 230 may be made as the rinsate from the cleaning process is drained from the vessel 22 at the end of the default cleaning process to verify in real-time the level of contaminant on-site without the need to send out a physical sample. In alternative embodiments, the cleaning process may be accomplished using a fluid recirculation process as described for the cleaning of a spray tank on a farm in FIGS. 5-6.

Figure 8:
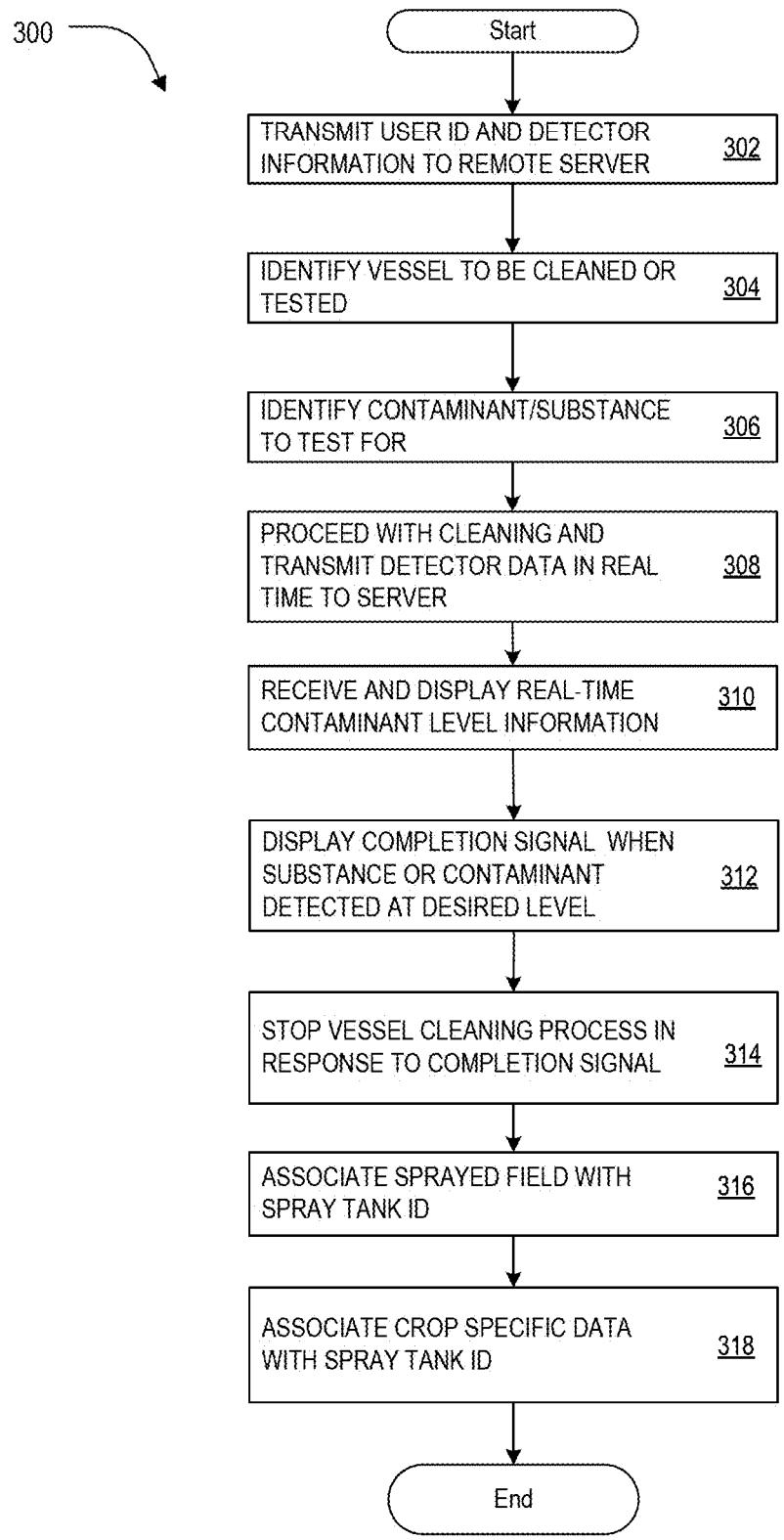
FIG. 8 is a flow diagram of a method for detecting contaminant levels and tracking certification-related data executable in the system of FIG. 1.

One embodiment of a method 300 for cleaning and verifying decontamination of a vessel, for example of a spray tank or similar vessel being used on a farm, using the systems described above is illustrated in FIG. 8. Using a handheld system such as illustrated in FIG. 1, the farmer may first enter a user identifier (ID) in the mobile device and the mobile device transmits that information to the remote server for authentication, along with automatically appending information on the detector 12, which may include probe and/or detection circuitry identifying information (at 302). The probe and/or detection circuitry identifying information may include serial number information for the probe 20 and detection circuitry 22, the Media Access Control (MAC) address for each and the Internet protocol (IP) network address. After receiving and transmitting data at the mobile device for authenticating the user, detector 12 and mobile device 18, the farmer may enter identifying information for the spray tank or other vessel being cleaned (at 304). The spray tank may have a scannable code, such as an optically scannable bar code or QR code affixed to it that may be automatically scanned with the mobile device. Any of a number of other spray tank or other vessel identifier labelling techniques, such as radio frequency identifiers (RFIDs) and so on may be used. Alternatively, a unique serial number, code or other identifier associated with the spray tank may be manually entered into the mobile device 18 and transmitted to the remote server 26. Additionally, the farmer may use the mobile device to scan in or manually enter one or more substance/contaminant identifiers, such as a Universal Product Code (UPC) for the one or more substances, to inform the remote server of the one or more contaminants that the sensor will be providing data on during the spray tank cleaning process (at 306). The mobile device 18 may also include geolocation information in its communications with the server, either from a GPS sensor included in the mobile device 18 or a GPS software function capable of generating the location of the mobile device in cooperation with a cellular or other communication network in communication with the mobile device. Alternatively, or in addition, the mobile device may transmit a farm identifier entered by the user or determined by the GPS position of the mobile device.

After authenticating the user and equipment information, and assuming that the server does not identify a mismatch in the probe capability and the type of contaminant or substance to be tested, or any other user, device or location authenticity issue, the cleaning process may be started, for example using a set-up such as shown in Example 1 above, where the rinsate material is cycled through the spray tank and any associated equipment and real-time data from the probe and detection circuitry of the detector are transmitted to the mobile device 18. The mobile device 18 transmits the real-time data to the server and the server 26 processes the data in real-time to account for the age of the probe and probe type to determine contaminant levels (at 308). The ongoing contaminant level measurements may be transmitted back to the mobile device 18 and displayed by the mobile device 18 to the farmer or other user (at 310).

Once the server 26 determines from the detector data that the contaminant level is low enough to meet the desired standard, the server 26 may transmit a completion signal to the mobile device 18 that may be displayed to the farmer (at 312) and prompts the farmer to then shut-off the cleaning process (314). The mobile device 18 or server 26 may then associate the sprayed field ID with the spray tank ID (at 316), as well as associate the crop specific data, such as lot ID and type, with the spray tank ID (at 318) in the historical test data record of the data storage layer in the server.

Although the data transfer for the sensed contamination information for the detector 12 may be sent to the remote server 26 for processing, and the remote server may then analyze that data to determine contaminant level and immediately transmit back the contaminant level information and a completion signal to the mobile device 18, in other embodiments, the mobile device may calculate and display the contamination level information and generate the completion signal internally. In this alternative embodiment, the mobile device may still perform the steps of authenticating user ID, detector information, vessel identification and contaminant identification with the remote server 26 (steps 302, 304 and 306), but instead of then sending the raw sensed contaminant data to the server 26, the mobile device may internally identify and determine the contaminant level from the raw sensor data without transmitting it to the server 26. In this alternative embodiment, the algorithms for identifying contaminant level, for adjusting calculation based on probe or other detector information and for recognizing the point (e.g. a predetermined contaminant level threshold or predetermined contaminant level range) when a desired contaminant level has been reached may all be completed and generated at the mobile device itself. In order to implement this alternative embodiment, the memory of the mobile device may be pre-loaded with instructions for making the analysis, or the server 26 may transmit to the mobile device the instructions and other information for the mobile device to locally process the data in response to receiving the authentication and device identification information from the mobile device (steps 302-306).

In one alternative embodiment, the mobile device 18, may send a signal preventing operation of the cleaning process equipment, such as the pumps that flush rinsate through the spray tank and spray arm described in Example 1 above, if there is a mismatch or other irregularity in the authentication information (user ID, geolocation information, etc.) provided to the server with the information contained in the server. For example, if the server determines from the contaminant identifying information and the probe or other sensor identifying information that the probe 20 (or probes) is not suited to test for the contaminant, then the server may send a signal notifying the user not to start the process. Alternatively, the server may send a command or instructions to the mobile device that is relayed to the cleaning equipment, to shut-off a power switch or other lockout device of the cleaning equipment to prevent the cleaning process from starting or continuing. In a variation of the above alternative, the mobile device 18 may receive the authentication or compatibility error from the server and determine locally to generate and send the power shut down command to the cleaning equipment.

In another embodiment, this automatic control of the cleaning process may be applied when a cleaning process has already started. For example, when the completion signal is received from the server for the decontamination process that is being monitored in real time (for example at steps 312 and 314 of FIG. 8) this same power shut down code capability may be used, where the completion signal of step 14 is either accompanied by a command to be forward by the mobile device to shut down the cleaning process, or by instructions for the mobile device to generate its own shut-down command to automatically stop the cleaning process, rather than simply waiting for the farmer to shut down the equipment after receiving the displayed completion notification.

Figure 9:
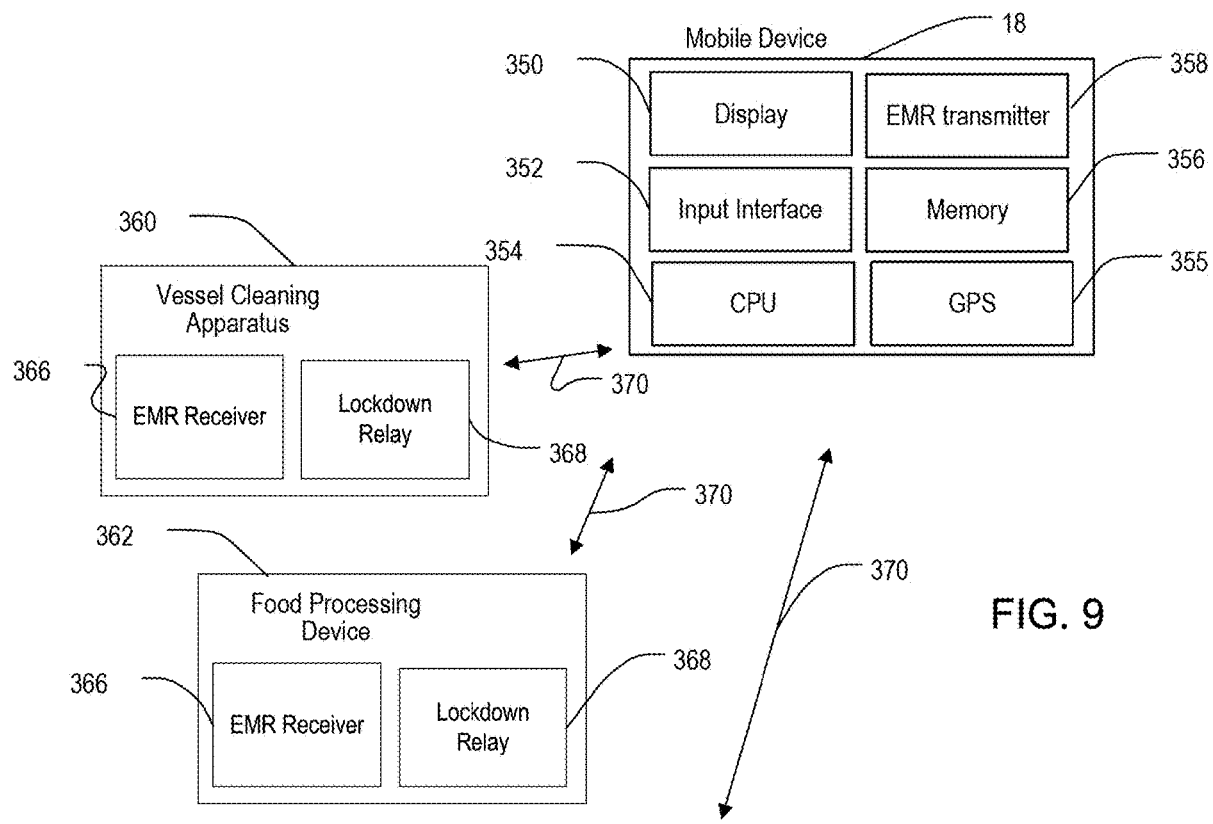
FIG. 9 illustrates a mobile device of the detector system of FIG. 1 and exemplary chemical processing, food processing and vessel cleaning equipment controllable by the mobile device in one embodiment.

In various embodiments, the detection system 10, or at least the mobile device 18 of the system 10, may be interlocked with equipment to shut down any equipment involved in any portion of the overall process of managing the flow of chemicals and food, not just at the farm level or limited to shutting down the cleaning process automatically as described above. Referring to FIG. 9, in one implementation, the interlock-enabled system and process consists of the detection system 10, for example the mobile device 18 of the detection system 10, having a suitable electromagnetic radiation (EMR) transmitter, for example radio frequency, RFID, Wi-Fi, Bluetooth, cellular or optical technologies. The mobile device 18 may be a smartphone, tablet or other portable device having a display 350, user input interface 352, processor 354, GPS location function or sensor 355, memory 356 and one or more EMR transmitters 358. The equipment that mobile device 18 would be able to control based on the contaminant detection results may include the entirety or a part of a vessel cleaning apparatus 360 (e.g. the cleaning equipment on the farm used to clean the vessel as described above), a food processing device 362 at a food processing location, farm equipment 364 (such as a sprayer, tractor or other farm implement) at a farm, or any of a number of other pieces of equipment involved in the processing or movement of a chemical or food product near the mobile device 18. Any piece of equipment 360, 362, 364 controllable by the mobile device may include, either integrated in its circuitry or as a discrete add-on component, an EMR receiver 366 compatible with the EMR transmitter 358, and an EMR-activated relay 368.

As in the above example of automatically shutting down the cleaning process on the farm, the mobile device 18 of the detector system 10 may be programmed in memory 356 to send an EMR signal when sample results are within the specified range as determined locally or by the remote server. The EMR signal may be a direct wireless communication link 370 between mobile device and equipment 360, 362, 364 as illustrated, or may be via a communication path over one or more networks in communication with the equipment 360, 362, 364 and mobile device 18. Because the EMR receiver 366 is preferably linked to a relay 368 that controls the power to activate the connected equipment upon receipt of the signal, automated control of the particular equipment by the detection system 10 may be achieved. It is contemplated that the equipment that can be included in interlocked mode with the detection system may include shut-off valves, pumps, power control units, motors (tractors, farm equipment, conveyor belts, fork-lifts, etc.) and a variety of off/on switches available for industrial processes. Also, it is contemplated that the mobile device 18 would only be able to control the particular piece of equipment 360, 362, 364 located in geographical proximity to the mobile device based on the testing or authentication taking place at the processing stage where the user and mobile device are located. The various different pieces of equipment 360. 362, 364 illustrated in FIG. 9 are representative of the types of equipment the automated shut-down or lockout process may be applied and does not represent that all of these pieces of equipment must either be at the same geographical location or be simultaneously controllable by the shut-off command transmitted by a single mobile device.

In another embodiment, the more than one piece of equipment, or more than one part of a single piece of equipment, may be independently and concurrently controlled by remote commands from the mobile device 18. For example, if a cleaning process is taking place on a sprayer device on a farm, the sprayer device may include multiple sets of EMR receivers 366 and associated EMR activated relays 368, each controlling a different function of the sprayer device. The detection system 10 may control an EMR receiver and EMR activated relay associated with a pump on the sprayer to shut-off that pump and stop a cleaning process of a vessel on the sprayer in response to detecting that the contaminant of interest is at an acceptable level, while concurrently controlling another part of the sprayer, such as a valve connecting the vessel to the spray nozzles of the sprayer, to prevent any spraying operation of the sprayer until the contaminant of interest is at the acceptable level. Thus, both a shutdown of a cleaning process and a removal or initiation of a lockdown of the normal operation of the equipment may be controlled by signals automatically generated by the detection system 10 or passed on by the detection system from the server 26. In yet other embodiments, only the lockdown function to prevent of the equipment's normal function may be automatically controlled and the shut-off of the cleaning process may be accomplished manually upon receipt and display to the user of the completion notification as described above.

In addition to the ability for the detection system to automatically shut down equipment to prevent a contaminated vessel or product move forward in processing, a management override function is contemplated to release or reset the systems affected by a shutdown. In one implementation, it is contemplated that interlock (lockdown) activation when a contaminant level is too high may also trigger the detector system 10 to record the time and GPS location of the initiation and termination of signals for the shutdown. The mobile device 18 may store this locally in memory 356 and/or transmit this information to the remote server 26. When the interlock is triggered, the mobile device 18 may also concurrently generate and transmit a notification of the interlock activation to a management device or devices. The notification may be an automatically generated call, text, email or other communication and may include the time and location of the shutdown, as well as details on the user and specific equipment affected. If in reply an authorized management signal is subsequently received at the mobile device 18, the shutdown equipment may be released from the interlock shutdown command and resume operation.

An advantage of the mobile device 18 and portable detector 12 is that they can be used on location to send real-time data from the probe or probes to a remote server for interpretation in real-time. Alternatively, the real-time data from the probe(s) may be interpreted and processed locally at the mobile device to provide contaminant level information, rather than sending the data to the server for calculation of the contaminant levels. This real-time detection and local processing, or transmission and remote processing, of data during the cleaning process avoids the typical physical sample acquisition time and delay before next use of the spray tank or other vessel while the sample is sent to a lab. The farmer or user of the system, during a vessel cleaning process, may be able to use the real-time detection and certification of contaminant level to shut off the cleaning process at a point much earlier than a default process might require. This on-site detection and verification may also avoid the need to re-clean a tank or vessel that was cleaned with a default cleaning process but later received results from the physical sample that indicated more cleaning was necessary. Although the notification of completion of the process in real-time described above provides the opportunity to save on time and cleaning materials over a default cleaning process, an automated shut-off command may provide an even greater process improvement.

The alternative automated shut-off embodiments may avoid the need for a farmer to wait and keep looking at the displayed real-time contamination level results during a vessel cleaning process and, when the completion notification does arrive, manually shut down the cleaning process. In yet other embodiments, the system may include the ability to prevent farm equipment from using a tank or vessel that has not been cleaned or that has been cleaned, but not to a standard that the particular field on a farm, or farm as a whole (based on the geolocation of the tank and farm equipment) are registered in the server to require. In this embodiment, the farm equipment, such as a tractor or sprayer vehicle, includes a lockdown device that is capable of preventing or shutting down power to the vehicle, or at least power to the portion of the vehicle capable of distributing the contents of the vessel, if the vehicle attempts to use uncleaned, or improperly cleaned vessel.

As described previously, the probe 20 and detector circuitry 22 of a portable detector 12 that may be used in the detection system 10 described herein may be configured for measuring the presence of one or of multiple different chemicals/contaminants. An advantage of the detection system 10 and remote server 26 processing of real-time contaminant measurements is that certain substances, for example herbicides 2,4-D and dicamba can be difficult to differentiate with single sensors. Due to the ability of the detection system to detect and transmit information in real-time, difficult to distinguish substances such as these may be more successfully differentiated. Signals from different probes may be combined in the present system to allow the computation layer of the server to interpret the signals in real-time using a comparison algorithm based on pre-determined operating characteristics of the particular probe or probe technology:

TABLE 1

| Chemical | Probe 1 | Probe 2 |
| --- | --- | --- |
| 2,4-D | Strong | Strong |
| Dicamba | Weak | Strong | where the presence of a strong signal on both probes (each probe using a different technology) in a side-by-side real-time comparison allows the algorithm to identify 2, 4-D rather than dicamba, when a single reading from a probe like Probe 1 or Probe 2 in the above Table 1 would not be able to make the distinction. Other side-by-side comparisons of real-time signals from different probes allow differentiation of other chemicals that may typically be difficulty to detect otherwise. For example, if one probe is a molecularly imprinted polymer (MIP) type that can recognize two compounds in a certain compound family but not differentiate compounds within that compound family is used in conjunction with a more precise probe, such as an antibody-based probe that responds to a specific one of those two compounds in the compound family but not the other, than the algorithm may simply be a subtraction of the two probe outputs to determine the presence of the other of the two compounds.

Figure 10:
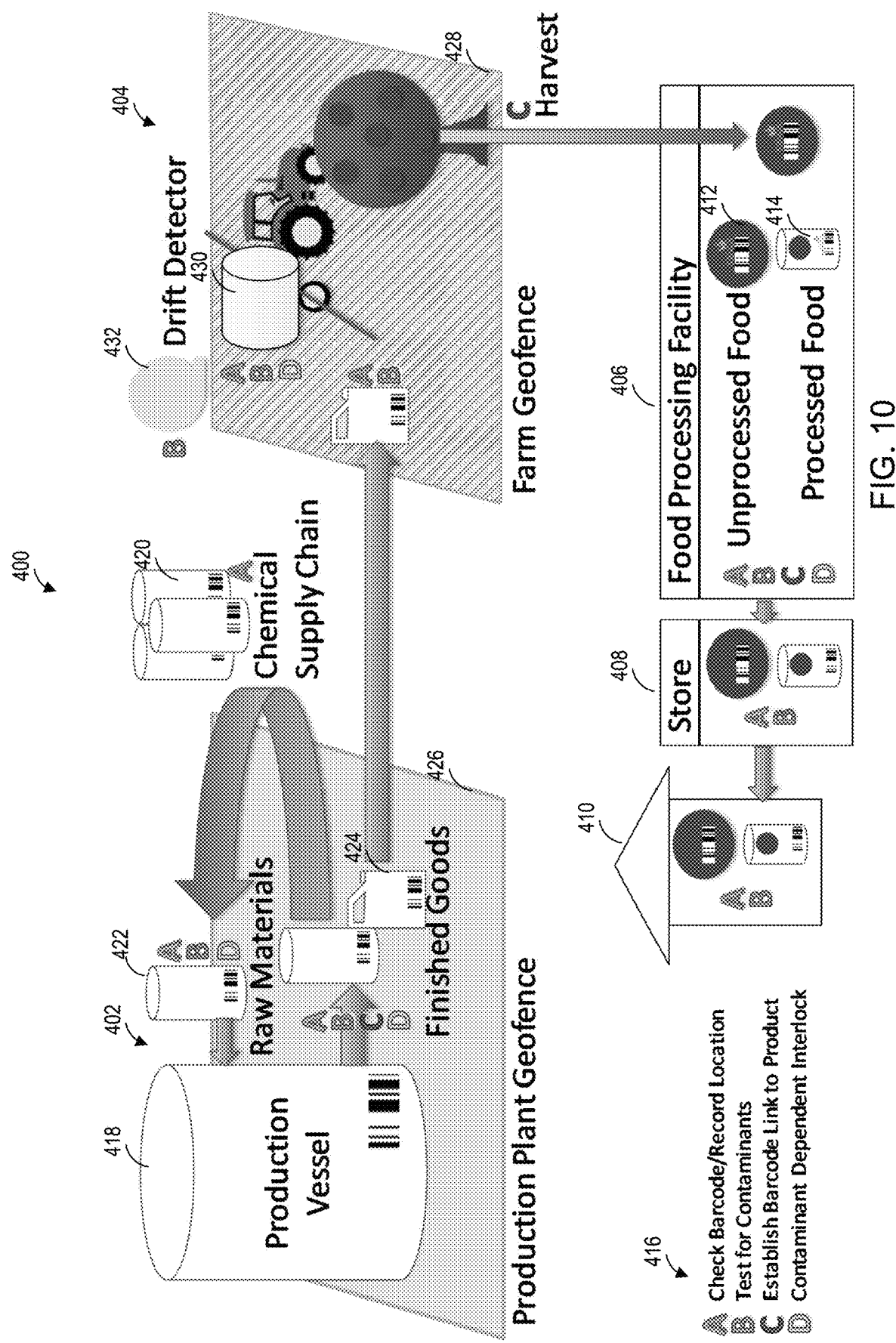
FIG. 10 is a flow diagram of a food safety processing flow utilizing the system of FIG. 1.

The above examples of a local, real-time contaminant detection and verification system are specific to vessels being tested on-site, for example at a farm where a farmer wishes to verify both that a chemical to be used is correct and accounted for, and to verify that the vessel is cleaned before reusing or storing that vessel. The systems and methods described herein, however, are adaptable for each of the stages of production. One example of a multi-stage production process 400 that may take advantage of the shown in FIG. 10. FIG. 10 represents a flow of food production from field to home, with tracking the food safety for a particular food product from production to the table. The first stage of the food production flow of FIG. 10 includes a production plant 402 where a chemical, such as a pesticide, is produced and introduced into the food production path. The second stage includes a farm 404 at which food is grown that uses the pesticide from the production plant 402. The third stage is a food processing facility 406 that receives the food harvested from the farm 404 and either prepares the harvested food for sale as unprocessed food 412 (e.g. whole apples) or prepares some form of processed food 414 (e.g. applesauce, apple pie) from the harvested food. The store 408 and the home 410 are represented as the final two stages of the food production flow 400. The overall food production flow with safety management that is illustrated in FIG. 10 is just one of many contemplated flows and greater or fewer stages may also be utilized in other implementations when tracking a product and contaminant levels.

Each of the stages in FIG. 10 may utilize the contaminant testing and tracking technique described above and utilize its own mobile device 18 and detector unit 12 to sample and receive real-time information on contaminant levels at each respective stage of the food production flow. A single central contaminant tracking service, represented in FIG. 1 as the server 26, may process and store information received from the different contaminant detection systems 10 at each stage (402, 404, 406, 408, 410) for multiple different entities. Thus, each stage may utilize a different detection system 10 (mobile device 18 and detector 12) suited for the specific type/level/granularity of contaminant measurement desired. All of the different detection systems 10 used may communicate over the one or more networks 24 between the respective system and the central server 26 that tracks the path of the chemical containing vessels and the product(s) exposed to the vessel contents, in the historical test data records section 56 in the data storage layer 48 of the server 26. In this manner, specific crop may be tracked, along with the chemicals and chemical containers that came into contact with it, and certified as satisfying a predetermined contaminant exposure level with accuracy and confidence. Although each stage of the production process in FIG. 10 may include the use of a separate detection system 10, the detection systems are not reproduced in FIG. 10 for ease of illustration.

Referring to FIG. 10, a process of using a system such as shown in FIG. 1, to certify the chemical supply chain of a chemical to be used with a crop is described. At the production plant 402, a user of the mobile device 18 first enters a user identification ID. When submitting the user ID, the mobile device also automatically transmits location and time stamp data for the mobile device and the hardware information relating to the detector unit 12 associated with the mobile device 18. The mobile device includes global positioning system (GPS) capability, for example via a standalone GPS sensor in the mobile device 18 or through use of GPS functionality available through a cellular network in communication with the mobile device. The mobile device 18 passes on this data via a wireless or wired network 24 to the tracking server 26. At the tracking server 26, the server verifies the user ID and matches the detector unit information to verify the capabilities of the probe and sensor circuitry in the detector unit. The detection system 10 in use at the production plant 402 may be used to verify the purity, in other words that the chemical product being produced is at a high enough concentration to indicate what is being produced is what is expected, and record the content of that tank with the server. After production of a batch of the chemical is finished and the tank is cleaned, the same detection system may then be used to detect that the production vessel is properly cleaned to a low enough level of that chemical before being used for another production process.

As illustrated in the legend 416 of FIG. 10, different combinations of barcode checking and location tracking (designated task "A"), contaminant testing (designated task "B"), new barcode association (designated task "C") and contaminant dependent interlock functionality (designated task "D"), may take place at each stage and within each stage. In the first stage 402, the chemical supplies 420 received into the production plant 402 are simply scanned, but those used as the raw materials 422 going into a product formulation (e.g. into production vessel 418) are scanned tested for contaminants, and production of the chemical product (e.g. pesticide) may be stopped (tasks A-D) if the detection system 10 identifies a contaminant in the raw materials. Similarly, the finished goods 424 from the production vessel 418 are processed through tasks A-D to track the path of the chemicals through production and prevent shipment if a contaminant is detected. A production plant geofence 426 may be used in conjunction with the GPS location capabilities of the mobile devices 18 used in the detection systems 10 to verify that the chemical products are at the chemical plant 402. At the next stage 404, the mobile device 18 of the detection system 10 located at the farm 404 scans in the incoming finished chemical goods (e.g. herbicide) and the previously established farm geofence 428 provides verification at the server that the expected chemicals 424 are received at the correct location, where they may be scanned and checked for contaminants. The chemical products may be used in a spray tank 430, where the spray tank 430 is tested, before and after use, as described previously. As discussed above, the lockout function at the farm 404 may be implemented as a shutdown of the sprayer and or the tractor carrying the sprayer if the sprayer is not cleaned or contains an undesirable contaminant based on the detector system measurements taken on site (tasks A, B and D). The farm stage also includes the creation of a new bar code or other identifier (task C) at harvest to link the harvested food to the specific chemicals used, the farm location and the testing history of the one or more vessels used in the process of growing and harvesting the food. Additional chemical exposure data may be provided to the system 100 at the farm stage 404 by one or more drift detectors 432 that can be located just inside or outside the field boundary (geofence) to determine if adjacent field herbicide or other chemical application drifted into the area of the crop being harvested. The location of the drift detector 432, the time of the measurements and the crop or lot identifier may be linked in the historical test data 56 of the server 26 based on a query to the drift detector 432 by a mobile device 18 that is in communication with the server 26.

In one embodiment, the geofence 426 at the production plant or the geofence 428 at the farm, may each be a plurality of separately identifiable geofences (previously determined and provided to the detection system 10 or server 26) that divide up the production facility or farm into separately identifiable sections. For example, the farm may include separate geofences for each different field so the location of equipment and chemicals can be tracked on a field-by-field basis. In this manner, a farmer will be able to specify that sprayer equipment, such as a spray rig, with the current chemicals is compatible for fields 1, 2 and 3 but not field 4, 5 and 6 until the spray rig has been certified as clean. Thus, the detection system 10 could either be configured to maintain a lockdown of the spraying operation capabilities of the spray rig for anywhere in the overall farm geofence until the vessel and/or other components of the spray rig are cleaned, or may be configured to lockdown the spraying operations of the spray rig on only pre-designated fields within the farm until the spray rig is certified as cleaned.

After being harvested, the lot or lots of harvested foods may be shipped to a food processing facility 46 as a next stage. The harvested lots may be lightly processed, such as basic washing and packing of fruits or vegetable, or may be prepared in a more processed form, such as a sauce or other prepared version of the harvested food. Whether prepared as unprocessed food 412 or processed food 414, each item or package is barcode detected, tested for contaminants, given a new barcode that is linked to the history of the prior one and, subject to a processing interlock feature (e.g. automatically signaling equipment at the food processing facility 406 to shut down, such as by shutting down a conveyor or preventing automated movement or shipment of a lot that fails a contaminant test (see task A-D). A detection system 10 that may be used at the processing facility 406 may be configured with appropriate probes to sample wash water used to rinse the fruits or vegetables and/or headspace gasses given off by the fruits or vegetables, for example. At the store stage 408 or home stage 410, a detection system 10 may also be used to check and record location data for the processed or unprocessed food, as well as to perform some testing for contaminants. As with the type of testing done at the food processing facility, the store and home tests may include testing wash water and or headspace gasses.

It is expected that the server may communicate with one or more of a regulatory server 28, insurance company server, food industry server or other authorized system to provide verification of measurements and procedures that the food has gone through. The communication may be in the form a token or other data structure at, which may be encrypted with a shared key for improved trust and validity, certifying that levels of toxins or contaminants measured fall within a predetermined range. These certifications or tokens may be locally stored at the server 26 upon receipt from the regulatory server or other certification source and accessible to stores and to consumers at their homes, by scanning the barcode or other identifier on the processed or unprocessed food, to bolster confidence in the quality level of the food. These certifications may be automatically transmitted by the server 26 to an insurer, association, cooperative or other interested and authorized party in response to a predefined milestone in processing of the food or chemical. For example any available certification token, and/or the historical data for the product (or chemical or vessel), may be triggered for transmission by the server in response to receipt at the server of a location change for the tracked food, chemical or vessel (chemical production facility to farm, farm to food processing facility and/or food processing facility to store transitions). The location change may be triggered by barcode scanning and geolocation data of the scanning device, such as a detection system 10, that reaches the server.

Figure 11:
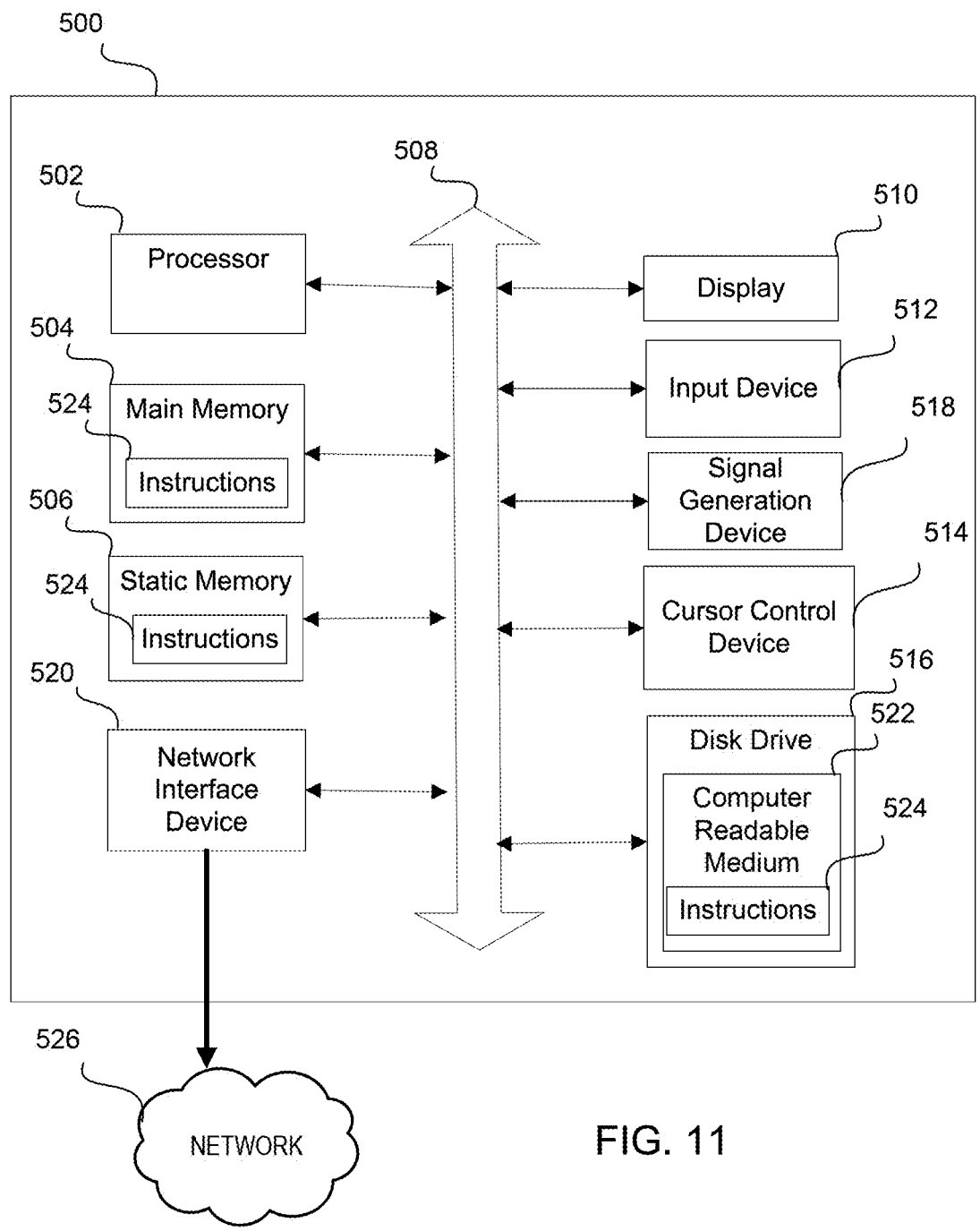
FIG. 11 illustrates a computer system which may be implemented in, or as, one or more parts of the system illustrated in FIG. 1.

Referring to FIG. 11, an illustrative embodiment of a general computer system that may be used in, or for, one or more of the components described above, or in any other system configured to carry out the methods discussed above, is shown and is designated 500. The computer system 500 can include a set of instructions that can be executed to cause the computer system 500 to perform any one or more of the methods or computer-based functions disclosed herein. The computer system 500 may be mobile or non-mobile, operate as a stand-alone device, or may be connected using a network, to other computer systems or peripheral devices.

In a networked deployment, the computer system may operate in the capacity of a server or as a client user computer in a server-client user network environment, or as a peer computer system in a peer-to-peer (or distributed) network environment. The computer system 500 can also be implemented as, or incorporated into, various devices, such as a personal computer ("PC"), a tablet PC, a set-top box ("STB"), a personal digital assistant ("PDA"), a mobile device such as a smart phone or tablet, a palmtop computer, a laptop computer, a desktop computer, a network router, switch or bridge, or any other machine capable of executing a set of instructions (sequential or otherwise) that specify actions to be taken by that machine. In a particular embodiment, the computer system 500 can be implemented using electronic devices that provide voice, video or data communication. Further, while a single computer system 500 is illustrated, the term "system" shall also be taken to include any collection of systems or sub-systems that individually or jointly execute a set, or multiple sets, of instructions to perform one or more computer functions.

As illustrated in FIG. 11, the computer system 500 may include a processor 502, such as a central processing unit ("CPU"), a graphics processing unit ("GPU"), or both. Moreover, the computer system 500 can include a main memory 504 and a static memory 506 that can communicate with each other via a bus 508. As shown, the computer system 500 may further include a video display unit 510, such as a liquid crystal display ("LCD"), an organic light emitting diode ("OLED"), a flat panel display, a solid state display, or a cathode ray tube ("CRT"). Additionally, the computer system 500 may include one or more input devices 512, such as a keyboard, scanner, digital camera or audio input device, and a cursor control device 514, such as a mouse. The computer system 500 can also include a memory unit 516, which may be a solid state or a disk drive memory, a signal generation device 518, such as a speaker or remote control, and a network interface device 520.

In a particular embodiment, as depicted in FIG. 11, the memory unit 516 may include a computer-readable medium 522 in which one or more sets of instructions 524, such as software, can be embedded. Further, the instructions 524 may embody one or more of the methods or logic as described herein. In a particular embodiment, the instructions 524 may reside completely, or at least partially, within the main memory 504, the static memory 506, and/or within the processor 502 during execution by the computer system 500. The main memory 504 and the processor 502 also may include computer-readable media.

In an alternative embodiment, dedicated hardware implementations, including application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

The present disclosure contemplates a computer-readable medium that includes instructions 524 or receives and executes instructions 524 responsive to a propagated signal; so that a device connected to a network 526 can communicate voice, video or data over the network 526. Further, the instructions 524 may be transmitted or received over the network 526 via the network interface device 520.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any tangible medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories, such as flash memory. Further, the computer-readable medium can be a random access memory or other volatile re-writable memory. Additionally, the computer-readable medium can include a magneto-optical or optical medium, such as a disk or tapes or other storage device to capture information communicated over a transmission medium. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

Although the present specification describes components and functions that may be implemented in particular embodiments with reference to particular standards and protocols commonly used by financial institutions, the invention is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

We claim:

1. A chemical contaminant detection system comprising:
   a portable detector having a probe and detector circuitry for detecting a predetermined contaminant in a fluid sample; and
   a mobile device configured to:
      wirelessly receive contaminant detection data from the portable detector and transmit the contaminant detection data from the portable detector to a remotely located processor in real-time; and
      receive and display on the mobile device real-time contaminant level data processed by the remotely located processor from the contaminant detection data.

2. The chemical contaminant detection system of claim 1, wherein the system is mobile and sized to be hand-held.

3. The chemical contaminant detection system of claim 1, wherein the portable detector comprises a plurality of probes, each of the probes configured to detect a different contaminant.

4. The chemical contaminant detection system of claim 1, wherein the portable detector is configured to receive the fluid sample from a rinsate collection apparatus connected to a vessel for containing fluid, during a cleaning process of the vessel.

5. The chemical contaminant detection system of claim 4, the mobile device is configured to receive and display a cleaning completion notification received from the remote processor in response to determination by the remote processor that the transmitted contaminant data indicates a contaminant level in the fluid sample has reached a predetermined level.

6. The chemical contaminant detection system of claim 5, wherein the mobile device is further configured to, in response to receiving the cleaning completion notification, automatically transmit a shut-off instruction to cleaning equipment being used in the cleaning process of the vessel.

7. The chemical contaminant detection system of claim 6, wherein subsequent to transmitting the shut-off instruction, the mobile device is configured to transmit a farm identifier and a crop identifier to the remotely located processor for association of a farm and a crop with the vessel at the remote server.

8. The chemical contaminant detection system of claim 2, wherein the mobile device is further configured to, in response to receiving real-time contaminant level data processed by the remote processor from the contaminant detection data, within a predetermined contaminant level range, automatically transmit a shut-off instruction to processing equipment in communication with the mobile device.

9. The chemical contaminant detection system of claim 2, wherein the mobile device is selected from the group consisting of a smartphone, tablet, and portable computer.

10. The chemical contaminant detection system of claim 3, wherein a mobile device is configured to:
   wirelessly receive contaminant detection data from the portable detector for each of the plurality of probes and to transmit the contaminant detection data from the portable detector to a remotely located processor in real-time;
   receive and display on the mobile device real-time contaminant level data for each of a plurality of different contaminants determined by the remote processor from the contaminant detection data for the plurality of probes.

11. A method of determining the level of chemical contaminant in a fluid sample, the method comprising the steps of:
   introducing a probe of a portable detector system into a fluid sample, wherein the probe is configured to detect at least one contaminant in the fluid sample;
   wirelessly transmitting contaminant detection signals from detection circuitry in communication with the probe to a mobile device of the portable detector system;
   transmitting, in real-time, the contaminant detection signals from the mobile device to a remotely located processing system;
   receiving, in response to the transmitted contaminant detection signals, real-time contaminant level data processed by the located processing system from the contaminant detection signals; and
   displaying the real-time contaminant level data to a user on a display of the mobile device.

12. The method of claim 11, wherein the fluid sample is taken from an agricultural spray tank located on a farm.

13. The method of claim 11, wherein the fluid sample is taken from an industrial mix tank or transportation tank.

14. The method of claim 11, wherein the fluid sample is taken during food processing at a food processing facility.

15. The method of claim 11, wherein the portable detector system comprises a plurality of probes, each of the probes configured to detect a different contaminant; and
   wherein the method further comprises concurrently transmitting contaminant detection signals from detection circuitry in communication with each of the plurality of probes to the mobile device of the portable detector system.

16. The method of claim 11, wherein introducing the probe of the portable detector system into the fluid sample comprises introducing the probe into rinsate from a rinsate collection apparatus connected to a vessel during a cleaning process on a farm.

17. The method of claim 16, further comprising receiving a cleaning completion notification from the remote processor in response to determination by the remote processor that the transmitted detection signals indicates a contaminant level in the fluid sample has reached a predetermined acceptable level.

18. The method of claim 17, further comprising the mobile device, in response to the cleaning completion message, transmitting a shut-off command configured to automatically shut of equipment being used in the cleaning process of the vessel.

19. A method for managing contaminant certification data based on real-time testing of contaminants at local stages of production of a product, the method comprising:
   in a system having a plurality of product handling facilities at different geographic locations, wherein each of a plurality of portable contaminant detection systems located at a respective one of the product handling facilities is in communication with a central contaminant tracking server, the central contaminant tracking server:
   receiving user and device identification from a portable contaminant detection system at one of the plurality of product handling facilities;
   receiving real-time contaminant detection data from the portable contaminant detection system;
   determining a contaminant type and a current contaminant level data from received the contaminant detection data;
   transmitting the current contaminant level data to the portable contaminant detection system for display at the portable contaminant detection system, wherein determining the contaminant type and transmitting the current contaminant level data is performed in real-time; and
   in response to determining that the current contamination level has reached a desired threshold, transmitting a completion notification to the portable contaminant detection system.

20. The method of claim 19, wherein the central contaminant tracking server transmitting a completion notification to the a portable contaminant detection system comprises:
   transmitting instructions to the portable contaminant detection system configured to cause the portable contaminant detection system to send a shut-off command to equipment at the one of the plurality of product handling facilities to cease a cleaning operation.

\* \* \* \* \*